United States Patent
Schmitt

(10) Patent No.: US 7,018,097 B2
(45) Date of Patent: Mar. 28, 2006

(54) X-RAY SUPPORT DEVICE

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/409,909

(22) Filed: Apr. 9, 2003

(65) Prior Publication Data

US 2004/0008820 A1 Jan. 15, 2004

(30) Foreign Application Priority Data

Apr. 11, 2002 (DE) .................. 102 15 982

(51) Int. Cl.
*H05G 1/02* (2006.01)
(52) U.S. Cl. ....................................... 378/197
(58) Field of Classification Search ................ 378/193, 378/195–198
See application file for complete search history.

(56) References Cited

U.S. PATENT DOCUMENTS

| | | | | |
|---|---|---|---|---|
| 4,412,346 A | * | 10/1983 | Takenouti et al. .......... 378/181 |
| 4,435,830 A | * | 3/1984 | Suzuki et al. ................ 378/197 |
| 4,541,293 A | * | 9/1985 | Caugant et al. ............ 74/89.18 |
| 5,050,204 A | * | 9/1991 | Siczek et al. ................ 378/197 |
| 5,515,416 A | * | 5/1996 | Siczek et al. ................ 378/197 |
| 5,521,957 A | * | 5/1996 | Hansen ........................ 378/198 |
| 6,092,928 A | * | 7/2000 | Mattson et al. ............. 378/205 |
| 6,155,713 A | * | 12/2000 | Watanabe .................... 378/197 |
| 6,382,833 B1 | * | 5/2002 | Leandersson et al. ....... 378/197 |
| 6,431,751 B1 | * | 8/2002 | Everett et al. ............... 378/197 |
| 6,461,039 B1 | | 10/2002 | Klotz et al. |
| 6,496,558 B1 | * | 12/2002 | Graumann .................... 378/39 |
| 6,733,176 B1 | * | 5/2004 | Schmitt ....................... 378/196 |
| 6,742,929 B1 | * | 6/2004 | Horbaschek ................ 378/197 |
| 6,872,000 B1 | * | 3/2005 | Atzinger .................... 378/197 |

FOREIGN PATENT DOCUMENTS

DE 199 47 809 A1 4/2001

* cited by examiner

Primary Examiner—Craig E. Church
Assistant Examiner—Thomas R. Artman
(74) Attorney, Agent, or Firm—Brinks Hofer Gilson & Lione

(57) ABSTRACT

An x-ray support device, including a radiation source and a radiation receiver, which are both movably supported on the ceiling either via a common support or each via separate supports, in which a support has a first boom rotatable about an essentially vertical pivot axis and extending essentially horizontally, and a second boom disposed rotatably about a vertical axis and extending essentially horizontally, on which the radiation source and/or the radiation receiver are supported directly or indirectly.

23 Claims, 2 Drawing Sheets

X-RAY SUPPORT DEVICE

REFERENCE TO RELATED APPLICATIONS

The present patent document claims priority to German Application Serial No. DE 10215982.3, filed Apr. 11, 2002, which is hereby incorporated by reference.

BACKGROUND

The invention relates to an x-ray support device, including a radiation source and a radiation receiver, both of which are supported movably on the ceiling via either a common support or each via separate supports.

Such x-ray support devices are known and serve to take radiographs of a patient on a patient bed or table, for which purpose the radiation source and the radiation receiver, for taking images, are oriented in stationary fashion relative to the patient. The displaceability, and thus the capability of positioning the radiation source and the radiation receiver relative to the patient, is an important criterion for the functioning of an x-ray support device, since radiographs are often be taken from various directions in order to perform various examination techniques or various types of examination.

SUMMARY

The object of the invention is to disclose an examination device in which the radiation source and the radiation receiver can be moved and positioned in manifold ways relative to a patient.

In an x-ray support device of the type described above, a support has a first boom, rotatable about an essentially vertical pivot axis and extending essentially horizontally, and a second boom, disposed rotatably about a vertical axis and extending essentially horizontally, on which the radiation source and/or the radiation receiver are supported directly or indirectly. The second boom is connected with or attached to the first boom.

The x-ray support device provides a support with two booms, and each boom can be rotated relative to the other. The radiation source and/or the radiation receiver is disposed on the second boom, so that by simply rotating the booms relative to one another, the radiation source and/or the radiation receiver can be put in an arbitrary number of different positions relative to the patient.

In a first embodiment, the first boom can be disposed nondisplaceably on the ceiling; that is, it is disposed in stationary fashion but rotatably on the ceiling. As an alternative, it is possible for the first boom to be displaceable essentially horizontally via a displacement system disposed on the ceiling; the displacement system includes a rail system, on which the first boom is supported displaceably via rollers or other slide device. The rail system itself, to further improve the adjustability, can have a first rail system and a second rail system with an essentially orthogonal displacement direction; the first boom is disposed displaceably on the first rail system. Thus, displaceability in the x-y direction is attained on the ceiling.

To further improve the mobility, the radiation source and/or the radiation receiver is supported longitudinally displaceably relative to the first boom, and/or the first boom is supported longitudinally displaceably on the second boom. Thus by this feature, a multifunctional movable system is disclosed which makes it possible to position, displace and rotate the radiation source and/or the radiation receiver.

In a first, especially advantageous variant, one common support for the radiation source and the radiation receiver is provided, and the radiation source and the radiation receiver are disposed on a C-curve bracket that is disposed on the second boom. This embodiment, using a C-curve bracket as a support for the radiation source and the radiation receiver, is advantageous especially for the sake of multifunctional mobility, because by suitable positioning of the C-curve bracket, the radiation source and the radiation receiver can be disposed on one side of the patient support table or the other. That is, the possibility exists of changing the side where the radiation source or the radiation receiver is located, and thus of varying the direction through which radiation passes, arbitrarily. This is highly advantageous, since in an x-ray examination it is often necessary to take images of the patient from various directions and thus in various projections.

The C-curve bracket itself can be disposed on the second boom via a vertical support; also, the C-curve bracket can be rotatable relative to the second boom about a vertical axis, optionally via the vertical support, and/or about a horizontal axis. These further rotation possibilities allow positioning that is even more versatile in terms of variation. The possibility also exists of providing a second C-curve bracket, coupled to the first C-curve bracket and essentially orthogonal to it, with a second radiation source and a second radiation receiver. Thus, a biplanar C-curve bracket device is achieved, in which both C-curve brackets and with them the respective radiation sources and radiation receivers can be positioned arbitrarily.

Along with the use of a common support and a C-curve bracket that carries the radiation source and the radiation receiver, in an alternative, the radiation source and the radiation receiver are each disposed on a separate support and are disposed rotatably on the respective second boom via a vertical support. In this alternative, the radiation source and the radiation receiver are accordingly supported separately.

The rotatability about the axis formed by the vertical support represents a further improvement in the positionability. The radiation source and/or the radiation receiver can each be disposed rotatably and/or tiltably relative to the vertical support. It is especially expedient, for the sake of changing the side of the patient support table that the radiation receiver or radiation source is on, if both supports are or can be positioned relative to one another in such a way that both the radiation source and the radiation receiver can be moved from one side to the opposite side, relative to the central longitudinal axis of a patient support device. In other words, supporting the two supports on the ceiling is selected especially in the case of a horizontal displaceability that is not achieved via a displacement system, such that the radiation source and the radiation receiver can be positioned on an arbitrary long side of the patient support table. The design of the supports should naturally be selected such that the respective longitudinal booms can be moved past one another without problems upon pivoting, even if they are disposed one above the other. It is also expedient in this connection if a vertical support that carries the radiation source or the radiation receiver is capable of telescoping.

BRIEF DESCRIPTION OF THE DRAWINGS

Further advantages, characteristics and details of the invention will become apparent from the exemplary embodiments described below and from the drawings. Shown are.

DETAILED DESCRIPTION OF THE DRAWINGS AND PRESENTLY PREFERRED EMBODIMENTS

Figure 1:
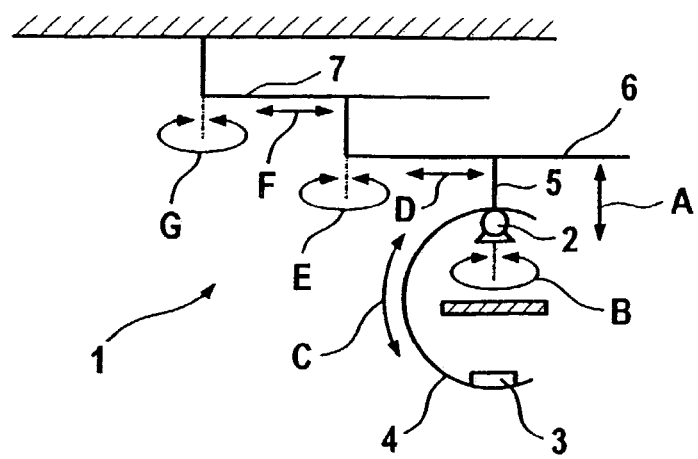
FIG. 1, a basic representation of an x-ray support device in a first embodiment.

FIG. 1 shows an x-ray support device 1, including a radiation source 2 and a radiation receiver 3, which are disposed jointly on a C-curve bracket 4. The C-curve bracket 4 in the example shown is disposed on a vertical support 5 (e.g. beam, girder, carrier or other support), which is capable of telescoping (see double arrow A). Relative to the vertical support 5, the C-curve bracket can be rotated on the one hand about the vertical axis—see double arrow B—and on the other the C-curve bracket is displaceable relative to itself along a curved path—see double arrow C.

The vertical support 5 in turn is disposed on a second boom 6 (e.g. cantilever, beam, gantry or other support) and is displaceable along it; see double arrow D. The second boom 6 is in turn rotatable on a first boom 7 (double arrow E) and is disposed longitudinally displaceably (double arrow F) on it. The first vertical support is in turn mounted rotatably (double arrow G) on the ceiling.

Figure 2:
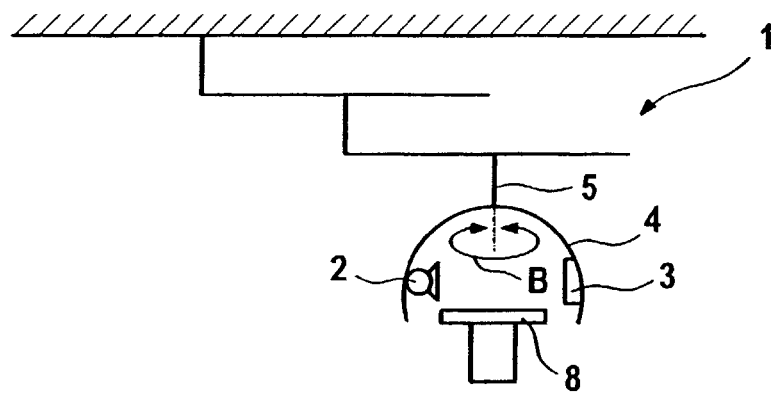
FIG. 2, the x-ray support device of FIG. 1, in a position that makes it possible to take images from the side.

As can be seen, the proposed supporting of the radiation source and the radiation receiver, that is, the C-curve, allows manifold possibilities in terms of motion because of the displacement axis and pivot axis realized, so that the radiation source and radiation receiver can be positioned virtually arbitrarily in space. This possibility is shown for instance in FIG. 2, where in addition to the x-ray device 1 of FIG. 1, a patient support table 8 is also shown. As can be seen, the C-curve bracket 4 has been displaced relative to the vertical support 5 such that the radiation source 2 is positioned on the left of the patient support table 8, and the radiation receiver 3 is positioned on the right of the patient support table 8. By simple rotation about the vertical axis (double arrow B) formed via the vertical support 5, the radiation direction can be transposed; that is, the radiation source 2 can be moved to the right side and the radiation receiver 3 to the left side of the patient support table.

Figure 3:
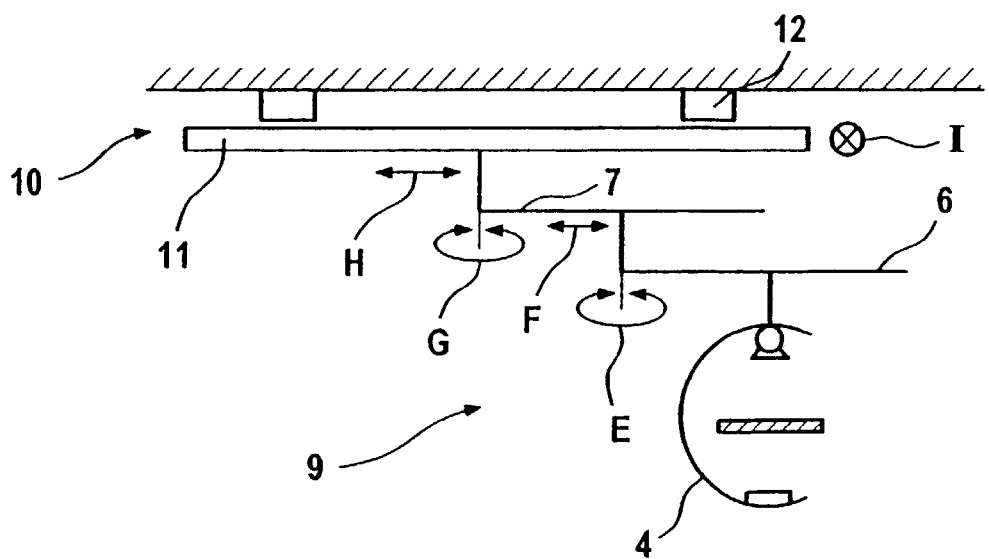
FIG. 3, the x-ray support device of FIG. 1, with a displacement system on the ceiling.

FIG. 3 shows a further x-ray support device, which up to this point similar to the x-ray support device 1 of FIG. 1. Here, however, the first vertical support for the boom 7 is disposed on a displacement system 10. The displacement system 10 includes a first rail system 11, on which the first boom 7 is disposed rotatably (double arrow G) and longitudinally displaceably (double arrow H). The first rail system 11 is in turn, as indicated by the cross or normal axis symbol I, displaceable on a second rail system 12 disposed on the ceiling. Overall, an x-y displaceability is achieved; that is, the mobility for adjusting the positioning of the radiation source 2 and the radiation receiver 3 is even more comprehensive, extensive or has an even greater scope.

Figure 4:
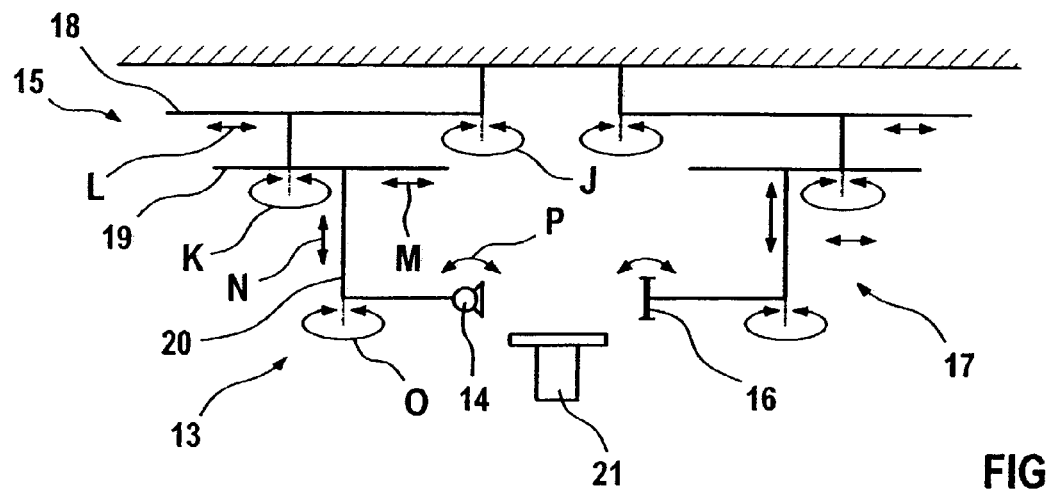
FIG. 4, a second embodiment of an x-ray support device with separate supports that carry the radiation source and the radiation receiver.

FIG. 4 shows a further embodiment of an x-ray support device 13 or system. The radiation source 14 is disposed on a separate support 15, and the radiation receiver 16 is disposed on a separate support 17. The individual supports 15, 17 (e.g., tripod, steadying device, beam, girder, gantry or other support) each include a first boom 18, which is disposed on the ceiling and is rotatable about its fastening point (double arrow J), and a second boom 19, which is rotatable relative to the first boom (double arrow K) and is displaceable longitudinally on it (double arrow L). A vertical support 20 is disposed longitudinally displaceably (double arrow M) on the second boom 19, and the vertical support 20 is capable of telescoping (double arrow N). On this vertical support in turn, the radiation source 14 is rotatable about the vertical pivot axis (double arrow O) formed by the vertical support 20 and is tiltable relative to the vertical support (double arrow P). The support 17 is constructed accordingly.

Figure 5:
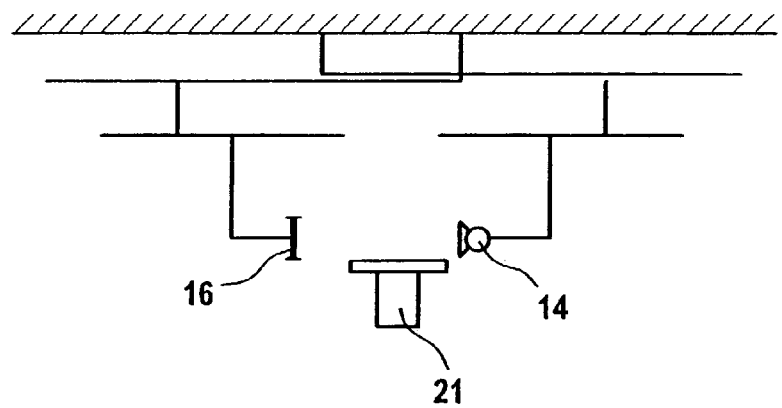
FIG. 5, the x-ray support device of FIG. 4, with the radiation source and radiation receiver disposed on the respective other sides of the patient support table.

This construction also makes it possible—see FIG. 5—to vary the lateral positioning of the radiation source 14 and radiation receiver 16 relative to a patient support table 21. As can be seen, the two supports 15, 17 are designed such that the respective booms can be moved past one another. Once again, the radiation direction and thus the projection direction can be varied without problems, and the telescopability and the tiltability of the radiation source 14 and radiation receiver 16 make an arbitrary positioning in terms of height and angle possible relative to the patient support table and thus to the patient.

Figure 6:
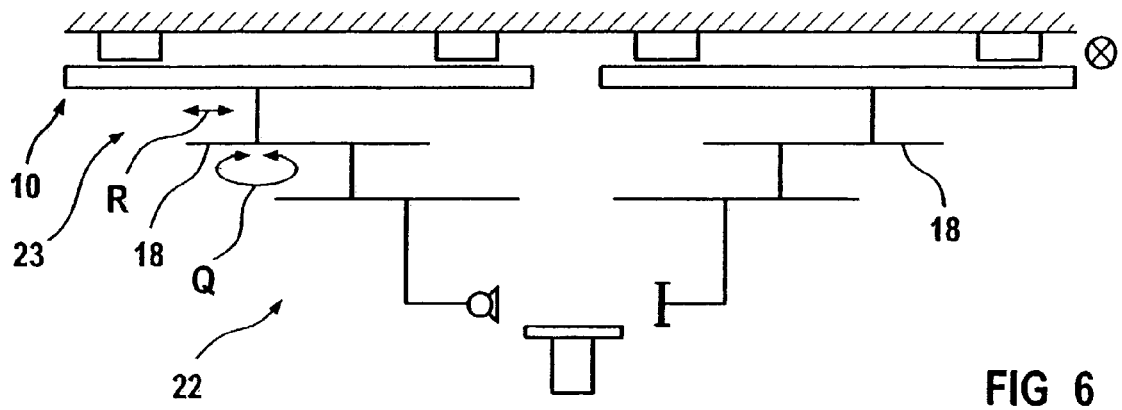
FIG. 6, the x-ray support device of FIG. 4, in which each support is supported displaceably via a displacement system on the ceiling.

FIG. 6, finally, shows an x-ray support device 22, which to this extent is similar to the x-ray support device 13 of FIG. 4. However, once again each of the first booms 18 is disposed rotatably (double arrow Q) and longitudinally displaceably (double arrow R) on its own displacement system 23, which is embodied like the displacement system 10 and makes an x-y displaceability possible.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

What is claimed is:

1. An x ray support device comprising a radiation source and a radiation receiver which are both supported movably on the ceiling by either one of: a common support or separate supports, characterized in that at least one support has a first boom, rotatable about an essentially vertical pivot axis and extending essentially horizontally, and a second boom connected with the first boom, the second boom disposed rotatably about a vertical axis and extending essentially horizontally and supported longitudinally displaceably on the first boom, at least one of the radiation source, the radiation receiver and both the radiation source and receiver are supported on the second boom and rotatable about a vertical pivot axis relative to the second boom.

2. The x ray support device of claim 1 characterized in that the first boom is disposed nondisplaceably on the ceiling.

3. The x ray support device of claim 1 characterized in that the first boom is displaceable essentially horizontally via a displacement system disposed on the ceiling.

4. The x ray support device of claim 3 characterized in that the displacement system includes a rail system on which the first boom is disposed displaceably.

5. The x ray support device of claim 4 characterized in that the rail system comprises a first rail system disposed on a second rail system with an essentially orthogonal displacement direction to the first rail system.

6. The x ray support device of claim 1 characterized in that at least one of:
the radiation source and the radiation receiver is supported longitudinally displaceably relative to the second boom.

7. The x ray support device of claim 1 characterized in that one common support is provided, and the radiation source and the radiation receiver are disposed on a C curve bracket that is disposed on the second boom.

8. The x ray support device of claim 7 characterized in that the C curve bracket is disposed on the second boom via a vertical support.

9. The x ray support device of claim 7 characterized in that relative to the second boom, the C curve bracket is at least one of: rotatable about a horizontal axis, displaceable along a curved path and combinations thereof.

10. The x ray support device of claim 7 characterized in that the C curve bracket comprises a first C curve bracket, wherein a second C curve bracket coupled to the first C curve bracket and essentially orthogonal to the first C curve bracket is provided with a second radiation source and a second radiation receiver.

11. The x ray support device of claim 7 characterized in that the one common boom housing support is capable of telescoping.

12. The x ray support device of claim 1 characterized in that the radiation source and the radiation receiver are each disposed on separate supports and are each disposed rotatably on the respective second boom via a respective vertical support.

13. The x ray support device of claim 12 characterized in that the radiation source and/or the radiation receiver are disposed rotatably and/or tiltably relative to the respective vertical support.

14. The x ray support device of claim 12 characterized in that both of the separate supports are positionable relative to one another in such a way that both the radiation source and the radiation receiver may be moved from one side to the opposite side, relative to the central longitudinal axis of a patient support device.

15. The x ray support device of claim 12 characterized in that one vertical support is capable of telescoping.

16. The x ray support device of claim 12 characterized in that at least one of: the radiation source and the radiation receiver is supported longitudinally displaceably relative to the second boom.

17. The x ray support device of claim 12 characterized in that the second boom is supported longitudinally displaceably on the first boom.

18. The x ray support device of claim 12 characterized in that at least one of: the radiation source and the radiation receiver is supported longitudinally displaceably relative to the second boom.

19. The x ray support device of claim 12 characterized in that the second boom is supported longitudinally displaceably on the first boom.

20. An x ray support device comprising:
a radiation source and a radiation receiver which are both supported movably on the ceiling by separate supports, characterized in that each of the separate supports has a first boom, rotatable about an essentially vertical pivot axis and extending essentially horizontally, and a second boom connected with the first boom, the second boom disposed rotatably about a vertical axis and extending essentially horizontally;
the second boom disposed rotatably about a vertical axis and extending essentially horizontally;
at least one of the radiation source, the radiation receiver and both the radiation source and receiver are supported on the second boom and rotatable about a vertical pivot axis relative to the second boom; and
wherein the radiation source and the radiation receiver are each disposed on separate supports and are each disposed rotatably on the respective second boom via a respective vertical support.

21. The x ray support device of claim 20 characterized in that the radiation source and/or the radiation receiver are disposed rotatably and/or tiltably relative to the respective vertical support.

22. The x ray support device of claim 20 characterized in that both of the separate supports are positionable relative to one another in such a way that both the radiation source and the radiation receiver may be moved from one side to the opposite side, relative to the central longitudinal axis of a patient support device.

23. The x ray support device of claim 20 characterized in that one vertical support is capable of telescoping.

* * * * *

UNITED STATES PATENT AND TRADEMARK OFFICE
CERTIFICATE OF CORRECTION

| | | |
|---|---|---|
| PATENT NO. | : 7,018,097 B2 | Page 1 of 1 |
| APPLICATION NO. | : 10/409909 | |
| DATED | : March 28, 2006 | |
| INVENTOR(S) | : Thomas Schmitt | |

It is certified that error appears in the above-identified patent and that said Letters Patent is hereby corrected as shown below:

Column 6, claim 20, lines 24-25, delete "the second boom disposed rotatably about a vertical axis and extending essentially horizontally;".

Signed and Sealed this

Sixteenth Day of March, 2010

David J. Kappos
*Director of the United States Patent and Trademark Office*